(12) United States Patent
Hoffman

(10) Patent No.: US 6,775,348 B2
(45) Date of Patent: Aug. 10, 2004

(54) FIBER OPTIC SCINTILLATOR WITH OPTICAL GAIN FOR A COMPUTED TOMOGRAPHY SYSTEM AND METHOD OF MANUFACTURING SAME

(75) Inventor: David M. Hoffman, New Berlin, WI (US)

(73) Assignee: General Electric Company, Milwaukee, WI (US)

( * ) Notice: Subject to any disclaimer, the term of this patent is extended or adjusted under 35 U.S.C. 154(b) by 0 days.

(21) Appl. No.: 09/683,888

(22) Filed: Feb. 27, 2002

(65) Prior Publication Data

US 2003/0161437 A1 Aug. 28, 2003

(51) Int. Cl.[7] .............................. G21K 1/12; H05G 1/64; G01T 1/20
(52) U.S. Cl. ..................... 378/19; 378/98.8; 250/367; 250/370.11
(58) Field of Search .......................... 378/19, 98.8, 57; 250/367, 370.11, 483.1; 359/341.5, 333

(56) References Cited

U.S. PATENT DOCUMENTS

| | | | | |
|---|---|---|---|---|
| 4,870,667 A | * | 9/1989 | Brunnett et al. ............... 378/19 |
| 5,103,099 A | * | 4/1992 | Bourdinaud et al. ......... 250/368 |
| 5,155,621 A | * | 10/1992 | Takeda et al. ............... 359/337 |
| 5,712,926 A | * | 1/1998 | Eberhard et al. ........... 382/205 |
| 5,831,269 A | * | 11/1998 | Nakamura et al. .......... 250/367 |
| 5,901,198 A | * | 5/1999 | Crawford et al. ............. 378/57 |
| 6,078,052 A | * | 6/2000 | DiFilippo .................... 250/367 |
| 6,087,665 A | * | 7/2000 | Hoffman et al. .......... 250/483.1 |
| 6,115,448 A | * | 9/2000 | Hoffman ....................... 378/19 |
| 6,310,352 B1 | * | 10/2001 | Gross et al. ........... 250/370.11 |
| 6,362,480 B1 | * | 3/2002 | Peter et al. .................. 250/366 |
| 6,553,092 B1 | * | 4/2003 | Mattson et al. ............... 378/19 |

* cited by examiner

Primary Examiner—Edward J. Glick
Assistant Examiner—Allen C. Ho
(74) Attorney, Agent, or Firm—Ziolkowski Patent Solutions Group, LLC; Michael A. Della Penna; Carl B. Horton (57) ABSTRACT

The present invention provides a detector for a CT system. The detector includes a scintillator with built-in gain for receiving and converting high frequency electromagnetic energy to light. Each scintillator is formed of a scintillating material and an optically stimulated material. The components may be intermixed with one another to form a single composite structure or formed into layers to form a single layered structure. The scintillator may be incorporated into the detector array of any CT system including medical diagnostic systems and package/baggage inspection systems.

27 Claims, 5 Drawing Sheets

FIBER OPTIC SCINTILLATOR WITH OPTICAL GAIN FOR A COMPUTED TOMOGRAPHY SYSTEM AND METHOD OF MANUFACTURING SAME

BACKGROUND OF INVENTION

The present invention relates generally to the detection and conversion of high frequency electromagnetic energy to electrical signals and, more particularly, to a scintillator array of fiber optic scintillators with optical gain for use with computed tomography systems.

Typically, in computed tomography (CT) imaging systems, an x-ray source emits a fan-shaped beam toward an object, such as a patient or a piece of luggage. The beam, after being attenuated by the object, impinges upon an array of radiation detectors. The intensity of the attenuated beam radiation received at the detector array is typically dependent upon the attenuation of the x-ray beam by the object. Each detector element of the detector array produces a separate electrical signal indicative of the attenuated beam received by each detector element. The electrical signals are transmitted to a data processing system for analysis which ultimately results in the formation of an image.

Generally, the x-ray source and the detector array are rotated about the gantry within an imaging plane and around the object. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to a data processing system.

Increasingly, there is a need for CT detector cells of reduced size. While reducing the relative size of each detector cell of a detector array has numerous advantages including increased CT system spatial resolution, reducing the size of each detector cell does result in some potentially detrimental effects. As the size of each cell is reduced, the light output/current output from each cell becomes increasingly small. In fact, the output signal from the cell can become so small that the signal is lost in the noise of the CT system's data acquisition system. Furthermore, as a result of this reduced signal output with decreased scintillator size, the scintillator material choices that the detector can be fabricated from become quite limiting. This also negatively affects the optimization and selection of subsequent properties like primary speed, x-ray quantum detection efficient, afterglow, etc.

It would therefore be desirable to have a detector with built-in optical gain thereby providing improved detector signal output to a data processing system of a CT system.

BRIEF DESCRIPTION OF INVENTION

The present invention is directed to a scintillator cell having optical gain overcoming the aforementioned drawbacks. The scintillator cell is comprised of material that yields a higher light output per absorbed x-ray photon thereby overcoming signal-to-noise limitations of data acquisition systems. As a result, the scintillator cell may also be comprised of a wider range of scintillator materials conducive to the optimization of other subsequent properties.

Therefore, in accordance with one aspect of the present invention, a fiber optic scintillator cell is provided. The fiber optic scintillator cell includes a first component formed of scintillating material and a second component formed of optically stimulated material.

In accordance with a further aspect of the present invention, a detector for a computed tomography system includes a fiber optic scintillator configured to receive high frequency electromagnetic energy having a first intensity and further configured to output light energy having a second intensity wherein the second intensity exceeds the first intensity. The detector further includes a photodiode optically coupled to the fiber optic scintillator and configured to detect the output from the fiber optic scintillator.

In accordance with yet a further aspect of the present invention, a computed tomography system is provided and includes a rotatable gantry having an opening to receive an object to be scanned. The system further includes a high frequency electromagnetic energy projection source configured to project a high frequency electromagnetic energy beam toward the object. A scintillator array having a plurality of scintillator cells is provided wherein each cell is configured to detect high frequency electromagnetic energy passing through the object. Each scintillator cell is further configured to output light having an intensity exceeding an intensity of the high frequency electromagnetic energy detected by the scintillator cell. The computed tomography system also includes a photodiode array optically coupled to the scintillator array and comprising a plurality of photodiodes. Each photodiode is configured to detect light output from a corresponding scintillator cell wherein each photodiode outputs a signal indicative of the light output of a corresponding scintillator cell. A data acquisition system (DAS) is connected to the photodiode array and configured to receive photodiode outputs. An image reconstructor is connected to the DAS and configured to reconstruct an image of the object from the photodiode outputs received by the DAS.

The present invention is also directed to a scintillator cell having improved light output characteristics. Therefore, in accordance with another aspect thereof, a method of manufacturing a fiber optic scintillator cell having optical gain is provided. A method includes the steps of fashioning a first component of scintillating material and fashioning a second component of optically stimulated material. The fiber optic scintillator cell may be manufactured by intermixing the first component and the second component in a single composite structure. The fiber optic scintillator cell may also be manufactured by forming the first component in a layer, forming the second component in a layer, and connecting the first component layer and the second component layer to one another in a single layered structure.

In accordance with yet another aspect of the present invention, a scintillator cell for use with a computed tomography imaging system is provided. The scintillator cell includes means for converting high frequency electromagnetic energy to light energy. The scintillator cell further includes means for amplifying the light energy output from the means for converting. The scintillator cell also includes means for outputting the amplified light energy to a light energy detector.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

The operating environment of the present invention is described with respect to a four-slice computed tomography (CT) system. However, it will be appreciated by those of ordinary skill in the art that the present invention is equally applicable for use with single-slice or other multi-slice configurations. Moreover, the present invention will be described with respect to the detection and conversion of x-rays. However, one of ordinary skill in the art will further appreciate, that the present invention is equally applicable for the detection and conversion of other high frequency electromagnetic energy.

Figure 1:
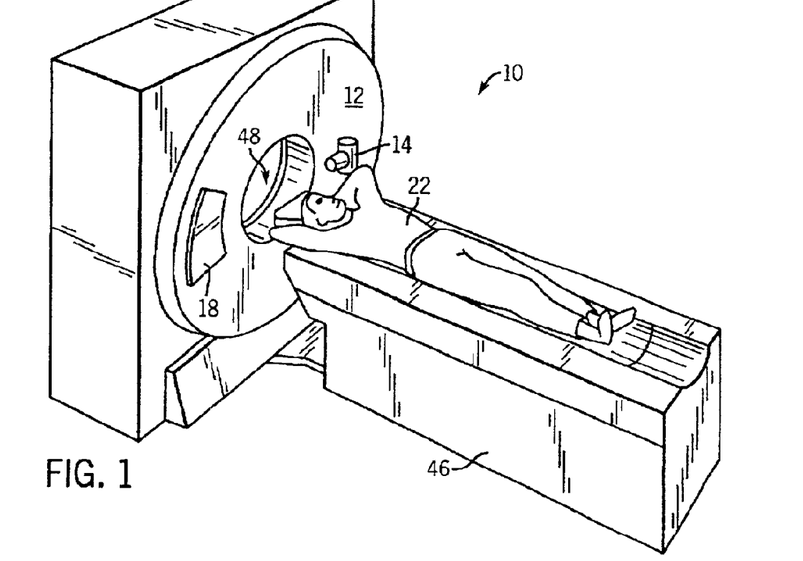
FIG. 1 is a pictorial view of a CT imaging system.
Figure 2:
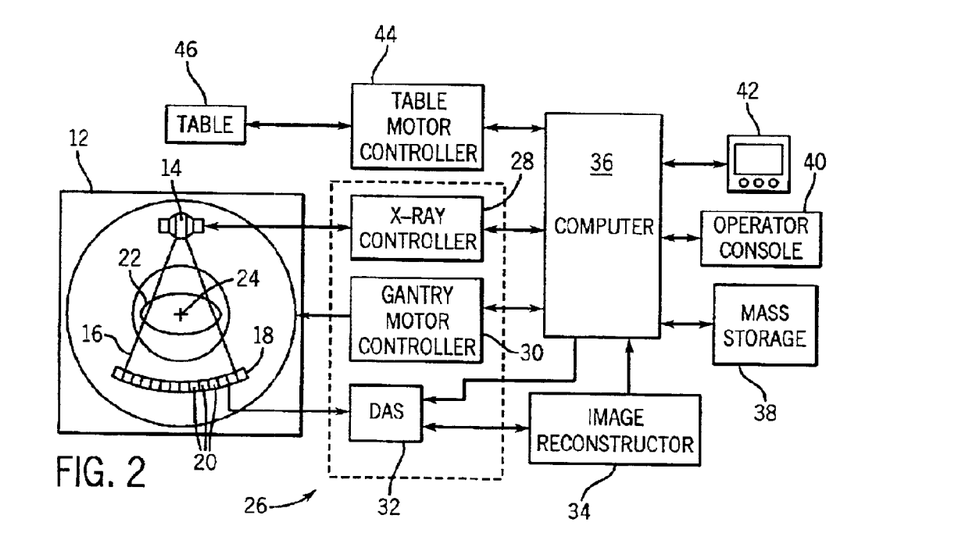
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Figures 3, 4:
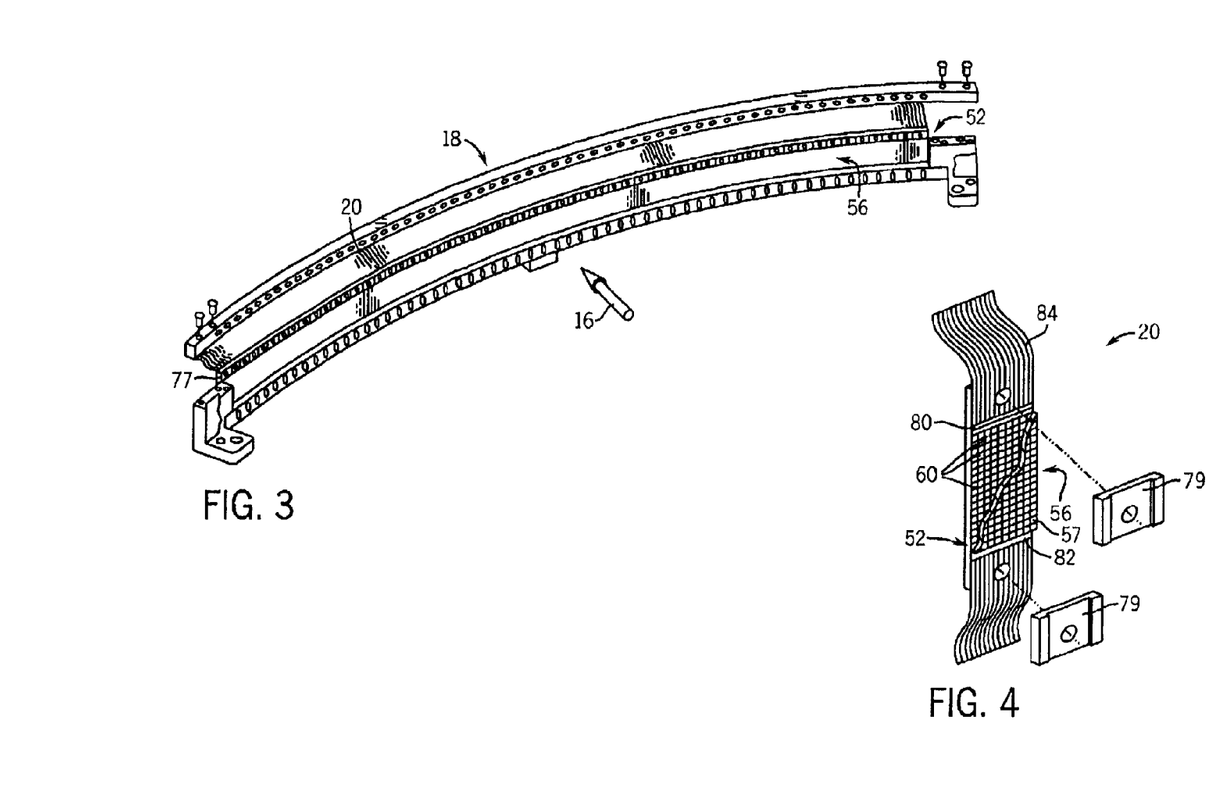
FIG. 3 is a perspective view of one embodiment of a CT system detector array.
FIG. 4 is a perspective view of one embodiment of a detector.

As shown in FIGS. 3 and 4, detector array 18 includes a plurality of scintillators 57 forming a scintillator array 56. A collimator (not shown) is positioned above scintillator array 56 to collimate x-ray beams 16 before such beams impinge upon scintillator array 56.

In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 84. Particularly, about one-half of photodiode outputs are electrically connected to switch 80 with the other one-half of photodiode outputs electrically connected to switch 82. Additionally, a reflector layer (not shown) may be interposed between each scintillator 57 to reduce light scattering from adjacent scintillators. Each detector 20 is secured to a detector frame 77, FIG. 3, by mounting brackets 79.

Switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

Figure 5:
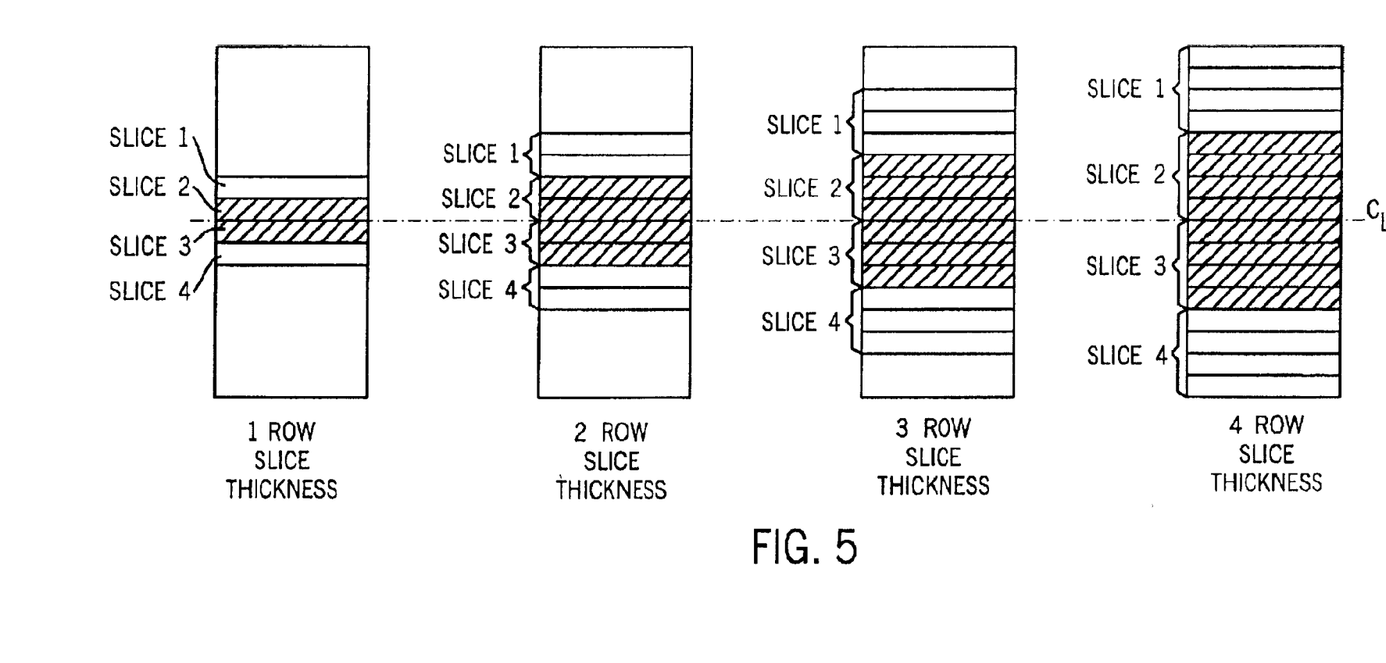
FIG. 5 is illustrative of various configurations of the detector in FIG. 4 in a four-slice mode.

As shown in FIG. 5, by transmitting the appropriate decoder instructions, switch arrays 80 and 82 can be configured in the four-slice mode so that the data is collected from four slices of one or more rows of photodiode array 52. Depending upon the specific configuration of switch arrays 80 and 82, various combinations of photodiodes 60 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

In a further embodiment, the present invention is directed to a scintillator cell formed partly of scintillating material and partly of optically stimulated material. As will be discussed with particular reference to FIGS. 6 and 7, the scintillator cell may be fashioned as a single fiber optic scintillator wherein the scintillating material and the optically stimulated material are intermixed with one another, or, in another embodiment, formed as a layered composite wherein the scintillating material and the optically stimulated material are discretely defined. The scintillating material may be comprised of conventional scintillator materials capable of absorbing high frequency electromagnetic energy, such as x-ray energy, at a high quantum detection efficiency which produces optical emissions in the form of light. Conventional scintillator materials include doped and undoped CsI, BGO, $CdWO_4$, and GOS. Additionally, a scintillator may be fabricated from other scintillator materials such as Highlight™ material, a product of the General Electric Company. The optically stimulated material may be comprised of those materials that may be pumped to an excited state by a laser or other means thereby yielding or triggering a cascading of multiple emissions. These multiple emissions from the optically stimulated component of the scintillator produces an optical signal intensity that exceeds the intensity of the light output produced by the first component of scintillator material. The optically stimulated material may be comprised of Erbium doped glass, such as that used in the fiber optic industry as a fiber optic amplifier. Other materials providing similar properties may be equivalently substituted. Such properties include means to produce increased gain similar to fiber optic amplifiers.

Figures 6, 7:
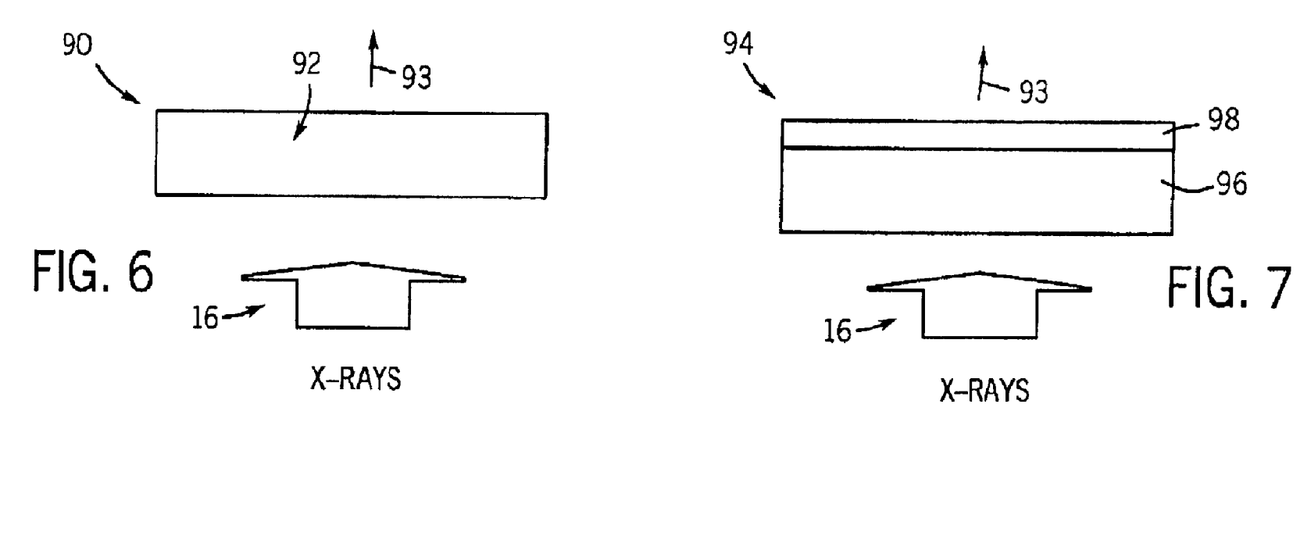
FIG. 6 is a cross-sectional view of one embodiment of the present invention.
FIG. 7 is a cross-sectional view of another embodiment of the present invention.

Referring now to FIG. 6, one embodiment of a scintillator cell is shown. In this embodiment, scintillator cell 90 is comprised of a first component of scintillator material and a second component of optically stimulated material which are intermixed with one another to form a single composite structure 92. Scintillator 90 is orientated such that x-rays 16 passing through an object to be scanned are converted and output as light energy 93. As indicated previously, the optically stimulated component amplifies the light energy generated by the scintillating component. That is, light energy generated by the first component of scintillating material has an intensity lower than the intensity of the light energy 93 output by scintillator cell 90.

Referring now to FIG. 7, another preferred embodiment of a scintillator cell is shown. In this embodiment, scintillator cell 94 is comprised of a first component of fiber optic scintillator material 96 and a second component of optically stimulated fiber optic material 98. Components 96 and 98 are arranged in layers and affixed to one another such that a layered scintillator cell results. Scintillator cell 94 is orientated such that component 96 receives x-rays 16 and component 98 affixed to component 96 outputs light energy 93 to a corresponding photodiode, FIG. 4. Scintillator cell 94 operates similarly to scintillator cell 90 of FIG. 6 in that scintillator component 96 converts x-ray 16 into light energy and thereby charges optically stimulated component 98 to a charged state thereby resulting in a cascading of multiple emissions of light energy. As a result, a large net intensity of light energy 93 is output in relation to the intensity of light energy generated by scintillator component 96. Component 98 thereby operates as an "amplifier".

Alternatively, scintillator cell 94 may be fabricated with a first layer of fiber optic scintillator material and a second layer of optically stimulated material. In this embodiment, the layer of optically stimulated material should be relatively thin to minimize light scattering within the scintillator cell. In another embodiment, the first component is fabricated from a thin layer of scintillating material and the second component is fabricated from optically stimulated fiber optic material. The layer of scintillator material should be a relatively thin layer so as to reduce or minimize light scattering within the scintillator cell.

A number of techniques may be employed to fabricate the several embodiments of the present invention. For example, an arrayed detector may be formed by stacking two uniform blocks of fiber optic scintillator material and optically stimulated fiber optic material. The stacked structure may then be diced or cut to form a number of pixilated cells forming a two-dimensional array similar to array 56 of FIG. 4. Following pixilation of the layered structure, a reflector material may be disposed between each pixilated cell to reduce light spreading between cells.

The present invention may be incorporated into a CT medical imaging device similar to that shown in FIG. 1. Alternatively, however, the present invention may also be incorporated into a non-invasive package or baggage inspection system, such as those used by postal inspection and airport security systems.

Figure 8:
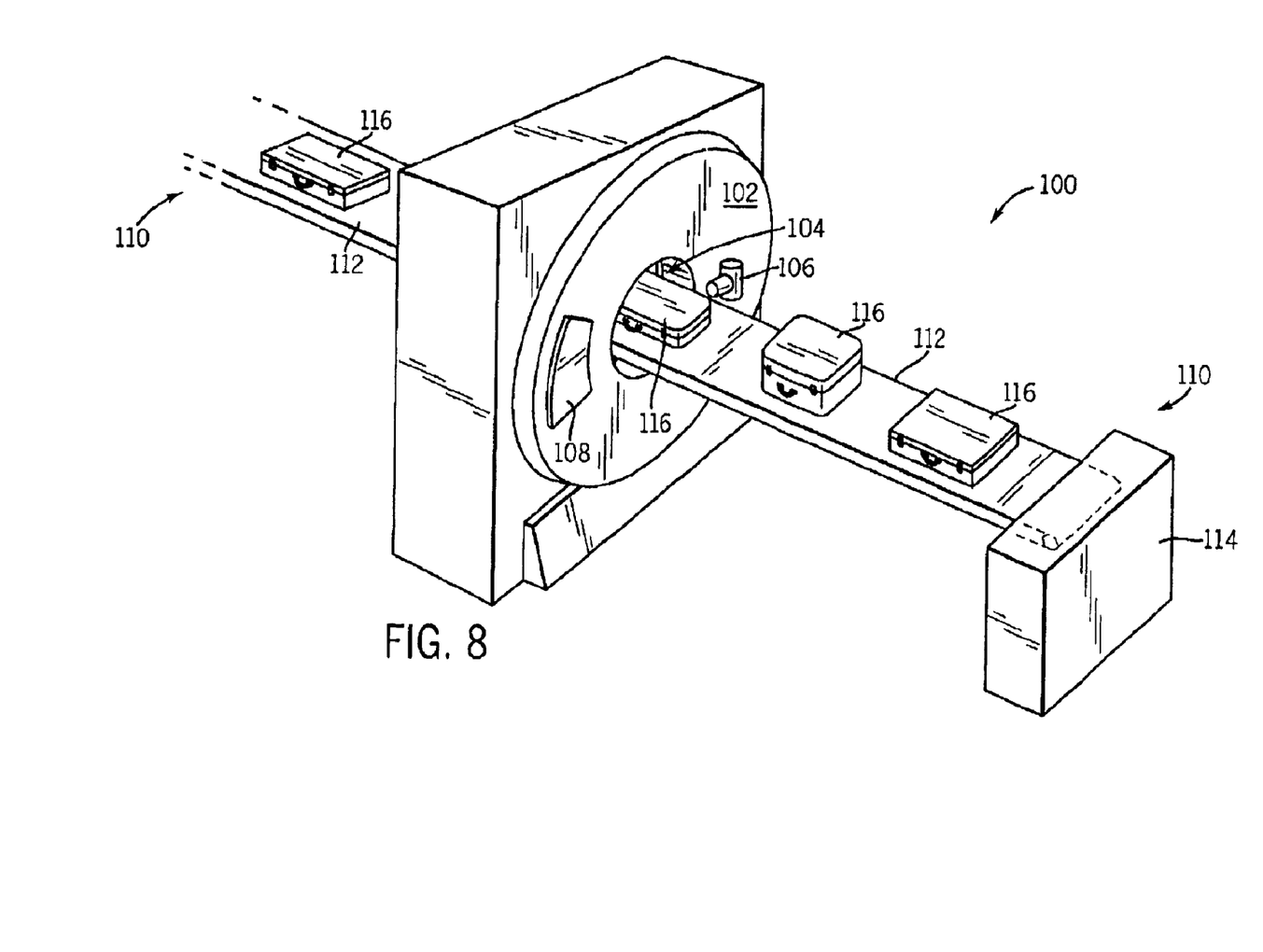
FIG. 8 is a pictorial view of a CT system for use with a non-invasive package inspection system.

Referring now to FIG. 8, package/baggage inspection system 100 includes a rotatable gantry 102 having an opening 104 therein through which packages or pieces of baggage may pass. The rotatable gantry 102 houses a high frequency electromagnetic energy source 106 as well as a detector assembly 108 having scintillator arrays comprised of scintillator cells similar to that shown in FIG. 6 or 7. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc.

Therefore, in accordance with one embodiment of the present invention, a fiber optic scintillator cell is provided. The fiber optic scintillator cell includes a first component formed of scintillating material and a second component formed of optically stimulated material.

In accordance with a further embodiment of the present invention, a detector for a computed tomography system includes a fiber optic scintillator configured to receive high frequency electromagnetic energy having a first intensity and further configured to output light energy having a second intensity wherein the second intensity exceeds the first intensity. The detector further includes a photodiode optically coupled to the fiber optic scintillator and configured to detect the output from the fiber optic scintillator.

In accordance with yet a further embodiment of the present invention, a computed tomography system is provided and includes a rotatable gantry having an opening to receive an object to be scanned. The system further includes a high frequency electromagnetic energy projection source configured to project a high frequency electromagnetic energy beam toward the object. A scintillator array having a plurality of scintillator cells is provided wherein each cell is configured to detect high frequency electromagnetic energy passing through the object. Each scintillator cell is further configured to output light having an intensity exceeding an intensity of the high frequency electromagnetic energy detected by the scintillator cell. The computed tomography system also includes a photodiode array optically coupled to the scintillator array and comprising a plurality of photodiodes. Each photodiode is configured to detect light output from a corresponding scintillator cell wherein each photodiode outputs a signal indicative of the light output of a corresponding scintillator cell. A data acquisition system (DAS) is connected to the photodiode array and configured to receive photodiode outputs. An image reconstructor is connected to the DAS and configured to reconstruct an image of the object from the photodiode outputs received by the DAS.

The present invention is also directed to a scintillator cell having improved light output characteristics. Therefore, in accordance with another embodiment thereof, a method of manufacturing a fiber optic scintillator cell having optical gain is provided. A method includes the steps of fashioning a first component of scintillating material and fashioning a second component of optically stimulated material. The fiber optic scintillator cell may be manufactured by intermixing the first component and the second component in a single composite structure. The fiber optic scintillator cell may also be manufactured by forming the first component in a layer, forming the second component in a layer, and connecting the first component layer and the second component layer to one another in a single layered structure.

In accordance with yet another embodiment of the present invention, a scintillator cell for use with a computed tomography imaging system is provided. The scintillator cell includes means for converting high frequency electromagnetic energy to light energy. The scintillator cell further includes means for amplifying the light energy output from the means for converting. The scintillator cell also includes means for outputting the amplified light energy to a light energy detector.

A scintillator cell with optical gain is provided. The scintillator cell is comprised of a first component of scintillating material and a second component of optically stimulated material. A scintillator cell may be fabricated in array that may be used with a detector assembly of a medical imaging device or a non-invasive package inspection device.

The present invention has been described in terms of the preferred embodiment, and it is recognized that equivalents, alternatives, and modifications, aside from those expressly stated, are possible and within the scope of the appending claims.

What is claimed is:

1. A fiber optic scintillator cell comprising:
   a first component formed of a block of scintillating material, the scintillating material configured to output light in response to electromagnetic energy incidence thereon;
   a second component formed of a block of optically stimulatable material, the optically stimulatable material configured to receive the light output from the block of scintillating material along a path substantially parallel to a path of electromagnetic energy incidence on the block of scintillating material and output light in a direction substantially parallel to the path of electromagnetic energy incidence, and further configured to output light at an intensity greeter than that output by the block of scintillating material; and
   wherein the first component and the second component are arranged in a discretely layered stack.

2. The fiber optic scintillator cell of claim 1 wherein the optically stimulatable materiel comprises material chargeable to an excited state.

3. The fiber optic scintillator cell of claim 2 wherein the scintillating material comprises material capable of absorbing electromagnetic energy and outputting optical emissions in response thereto and wherein the optical emissions cause the second component to output a signal having an intensity exceeding an intensity of the optical emissions received from the first component.

4. The fiber optic scintillator cell of claim 3 wherein the optical emissions output from the first component and received by the second component causes a cascading of multiple emissions from the optically stimulatable material.

5. The fiber optic scintillator cell of claim 1 incorporated into a computed tomography medical imaging diagnostic device.

6. The fiber optic scintillator cell of claim 1 incorporated into a non-invasive baggage inspection device.

7. A detector for a computed tomography system, the detector comprising:
   a fiber optic scintillator configured to receive high frequency electromagnetic energy from a first direction and convert the high frequency electromagnetic energy to light energy having a first intensity, and further configured to output the light energy in a second direction generally parallel to the first direction at a second intensity, wherein the second intensity exceeds the first intensity; and
   a photodiode coupled to the scintillator generally perpendicular to both the first and second directions and configured to detect the light energy output from the fiber optic scintillator along a path that is generally parallel to a path of high energy electromagnetic energy incidence on the fiber optic scintillator.

8. The detector of claim 7 wherein the fiber optic scintillator comprises a mixture of scintillating material and optically stimulatable material.

9. The detector of claim 7 wherein the fiber optic scintillator comprises a layer of scintillating material and a layer of optically stimulatable material coupled to the layer of scintillating material.

10. The detector of claim 9 wherein the layer of scintillating material is oriented to receive the high frequency electromagnetic energy and the layer of optically stimulatable material is coupled to the photodiode.

11. The detector of claim 7 wherein the fiber optic scintillator has light intensity greater than that of a scintillator without built-in gain.

12. The detector of claim 7 incorporated into at least one of a computed tomography medical imaging device and a computed tomography baggage handling device.

13. The detector of claim 7, wherein the fiber optic scintillator and the photodiode are each a polyhedron.

14. A CT system comprising:
   a rotatable gantry having an opening to receive an object to be scanned;
   a high frequency electromagnetic energy projection source configured to project a high frequency electromagnetic energy beam toward the object along a projection path;
   a scintillator array having a plurality of scintillator cells wherein each cell is configured to detect high frequency electromagnetic energy passing through the object, wherein each cell is configured to initially convert high frequency electromagnetic energy to light energy having an intensity and output the light energy along a path generally parallel to the projection path at an intensity exceeding that initially generated;
   a photodiode array optically coupled to the scintillator array and comprising a plurality of photodiodes configured to detect light output from a corresponding scintillator cell, wherein each photodiode outputs a signal indicative of the light output of the corresponding scintillator cell;
   a data acquisition system (DAS) connected to the photodiode array and configured to receive the photodiode outputs; and an image reconstructor connected to the DAS and configured to reconstruct a CT image of the object from the photodiode outputs received by the DAS.

15. The CT system of claim 14 further comprising a movable table configured to pass the object through the opening and wherein the object is a medical patient.

16. The CT system of claim 14 further comprising a conveyor system configured to pass the object through the opening and wherein the object is one of a package and a piece of baggage.

17. The CT system of claim 16 incorporated into at least one of a mail sorting facility and a baggage handling facility.

18. The CT system of claim 14 wherein each scintillator cell comprises a first component of scintillating material and a second component of optically stimulatable material.

19. The CT system of claim 18 wherein scintillating material includes material capable of triggering a cascading of emissions in the second component.

20. The CT system of claim 18 wherein the first component and the second component are intermixed with one another forming a single composite structure.

21. The CT system of claim 18 wherein the scintillator comprises a layer of the first component and a layer of the second component coupled to the layer of the first component.

22. A method of manufacturing a fiber optic scintillator cell having optical gain, the method comprising the steps of:
fashioning a first component of scintillating material;
fashioning a second component of optically stimulatable material; and
forming the first component in a single layer, forming the second component in a single layer, and connecting the first component layer and the second component layer to one another in a discretely layered structure.

23. The method of claim 22 wherein the second component comprises optically stimulatable material capable of emitting light having an intensity exceeding an intensity of light output by the first component.

24. The method of claim 22 further comprising the step of configuring the second component of optically stimulatable material from a material capable of being changed to an excited state by a laser.

25. A detector for a CT system, the detector comprising:
a pixilated array of scintillation elements arranged to receive x-rays emitted along on x-ray path from an x-ray emitter toward a subject to be scanned, wherein each scintillator element includes a first component formed of scintillating material and a second component formed of optically stimulatable material; and
a pixilated array of photodiodes coupled to receive light emissions from the pixilated array of scintillation elements along a direction generally parallel to the x-ray path such that each photodiode is configured to output a signal indicative of an intensity of light emitted by a corresponding scintillation element to a decoder.

26. The detector of claim 25 wherein the scintillating material comprises material capable of absorbing x-rays and outputting optical emissions in response thereto and wherein the optical emissions cause the second component to output a signal having an intensity exceeding an intensity of the optical emissions received by the first component.

27. The detector of claim 26, wherein the optical emissions output from the first component and received by the second component causes a cascading of multiple emissions from the optically stimulatable material.

* * * * *